US012621547B2

(12) United States Patent
Freeseman et al.

(10) Patent No.: US 12,621,547 B2
(45) Date of Patent: May 5, 2026

(54) VISUALIZATION DEVICE AND RELATED SYSTEMS AND METHODS

(71) Applicant: Boston Scientific Scimed, Inc., Maple Grove, MN (US)

(72) Inventors: Lance Adam Freeseman, Greenfield, MN (US); Danielle Frankson, Dayton, MN (US); Benn Horrisberger, Blaine, MN (US); Kenneth Gunter, Maple Grove, MN (US); Mark D. Wood, Sterling, MA (US); Paul D. Aquilino, Walpole, MA (US); James P. Rohl, Prescott, WI (US); James A Klos, Bay City, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 443 days.

(21) Appl. No.: 18/317,613

(22) Filed: May 15, 2023

(65) Prior Publication Data

US 2023/0283869 A1     Sep. 7, 2023

Related U.S. Application Data

(63) Continuation of application No. 16/853,010, filed on Apr. 20, 2020, now Pat. No. 11,689,789, which is a
(Continued)

(51) Int. Cl.
| | |
|---|---|
| *H04N 23/51* | (2023.01) |
| *A61B 1/05* | (2006.01) |
| *C23C 14/04* | (2006.01) |

| | |
|---|---|
| *C23C 14/08* | (2006.01) |
| *C23C 14/14* | (2006.01) |
| (Continued) | |

(52) U.S. Cl.
CPC ............... *H04N 23/51* (2023.01); *A61B 1/05* (2013.01); *C23C 14/042* (2013.01); *C23C 14/083* (2013.01); *C23C 14/14* (2013.01); *C23C 14/34* (2013.01); *H01J 37/32018* (2013.01); *H01J 37/32724* (2013.01); *H04N 23/50* (2023.01); *H04N 23/54* (2023.01)

(58) Field of Classification Search
CPC ........ H04N 23/51; H04N 23/50; H04N 23/54; A61B 1/05; C23C 14/042; C23C 14/083; C23C 14/14; C23C 14/34; H01J 37/32018; H01J 37/32724
See application file for complete search history.

(56) References Cited

U.S. PATENT DOCUMENTS

| | | | |
|---|---|---|---|
| 3,485,739 | A | 12/1969 | Toombs |
| 6,323,072 | B1 | 11/2001 | Yamazaki et al. |
| (Continued) | | | |

*Primary Examiner* — Sinh Tran
*Assistant Examiner* — Zhenzhen Wu
(74) *Attorney, Agent, or Firm* — Bookoff McAndrews PLLC

(57) ABSTRACT

According to one aspect, a visualization device may include an image sensor, a lens for focusing light onto the image sensor, a first end, a second end opposite the first end, a lateral wall surface extending between the first end and the second end, and a coating on the lateral wall surface. The coating may include at least one of an electrically-insulating layer and a light-blocking layer, and may be deposited on the lateral wall surface using, for example, physical vapor deposition (PVD).

18 Claims, 5 Drawing Sheets

Related U.S. Application Data continuation of application No. 15/348,515, filed on Nov. 10, 2016, now Pat. No. 10,666,841.

(60) Provisional application No. 62/253,731, filed on Nov. 11, 2015.

(51) Int. Cl.

| | |
|---|---|
| *C23C 14/34* | (2006.01) |
| *H01J 37/32* | (2006.01) |
| *H04N 23/50* | (2023.01) |
| *H04N 23/54* | (2023.01) |

(56) References Cited

U.S. PATENT DOCUMENTS

| | | | |
|---|---|---|---|
| 8,610,823 | B2 | 12/2013 | Rossi et al. |
| 8,803,211 | B2 | 8/2014 | Nakatani et al. |
| 2002/0053672 | A1 | 5/2002 | Yamazaki et al. |
| 2003/0054178 | A1 | 3/2003 | Anzaki et al. |
| 2003/0077914 | A1* | 4/2003 | Le ....................... H01J 37/3408 |
| | | | 438/763 |
| 2004/0095645 | A1* | 5/2004 | Pellicori ................ G02B 5/285 |
| | | | 359/584 |
| 2006/0046347 | A1 | 3/2006 | Wood et al. |
| 2007/0120214 | A1 | 5/2007 | Cole |
| 2008/0231977 | A1 | 9/2008 | Schwaab et al. |
| 2008/0283887 | A1 | 11/2008 | Lee |
| 2009/0115891 | A1 | 5/2009 | Ryu et al. |
| 2009/0134483 | A1 | 5/2009 | Weng et al. |
| 2010/0006965 | A1 | 1/2010 | Shiung et al. |
| 2010/0085473 | A1 | 4/2010 | Shiung et al. |
| 2010/0240531 | A1 | 9/2010 | Neubert et al. |
| 2010/0252103 | A1 | 10/2010 | Yao et al. |
| 2011/0025909 | A1 | 2/2011 | Tsai |
| 2011/0032409 | A1 | 2/2011 | Rossi et al. |
| 2011/0049591 | A1 | 3/2011 | Nakatani et al. |
| 2011/0051390 | A1 | 3/2011 | Lin et al. |
| 2011/0248367 | A1 | 10/2011 | Yang et al. |
| 2011/0261550 | A1* | 10/2011 | Wong ..................... H01L 24/19 |
| | | | 264/272.17 |
| 2011/0286736 | A1 | 11/2011 | Aizawa et al. |
| 2012/0104529 | A1 | 5/2012 | Tanaka |
| 2012/0155854 | A1 | 6/2012 | Huang et al. |
| 2013/0142991 | A1 | 6/2013 | Cao et al. |
| 2013/0149450 | A1* | 6/2013 | Feuerstein ........... C23C 14/042 |
| | | | 118/500 |
| 2014/0049687 | A1 | 2/2014 | Rudmann |
| 2015/0062035 | A1* | 3/2015 | Choi ..................... G06F 3/047 |
| | | | 345/173 |
| 2015/0257631 | A1 | 9/2015 | Sasamoto et al. |
| 2015/0318325 | A1 | 11/2015 | Nabighian et al. |
| 2024/0337010 | A1* | 10/2024 | Oliver ................... G02B 7/023 |

* cited by examiner

VISUALIZATION DEVICE AND RELATED SYSTEMS AND METHODS

CROSS-REFERENCE TO RELATED APPLICATION

This application is a continuation of U.S. application Ser. No. 16/853,010, filed on Apr. 20, 2020, which is a continuation of U.S. application Ser. No. 15/348,515, filed on Nov. 10, 2016, now U.S. Pat. No. 10,666,841, which claims the benefit of priority under 35 U.S.C. § 119 to U.S. Provisional Patent Application No. 62/253,731, filed on Nov. 11, 2015, each of which is incorporated herein by reference in its entirety.

TECHNICAL FIELD

Various aspects of the present disclosure relate generally to a visualization device and related systems and methods. More specifically, the present disclosure relates to a visualization device that has a coating, related systems for facilitating application (via, e.g., deposition) of the coating, and method steps performed to facilitate application of the coating.

BACKGROUND

Unlike traditional open surgery, minimally invasive surgery may utilize small incisions or natural orifice entry points. This approach may result in a faster recovery, reduced pain, reduced blood loss, and less scarring, among other benefits. In some forms of minimally invasive surgery, a camera may be inserted into a subject via an incision or anatomical opening, and may be guided to a target area. At the target area, the camera may relay images to a user to provide the user with instantaneous feedback as the user performs a procedure on the subject.

One type of camera used for such procedures may have multiple components arranged in a layered configuration. Sidewalls of the camera may be coated with a light blocking paint to reduce light saturation through the sidewalls. With conventional cameras, the light blocking paint may not adhere well to the sidewalls, may require multiple layers to sufficiently block light, and/or may be difficult to apply consistently, thereby affecting camera performance and/or increasing the overall dimensions of the camera due to the thickness of the layers of paint. Improving the coating of the sidewalls may address one or more of the aforementioned issues and/or enhance camera performance.

SUMMARY

Aspects of the present disclosure relate to, among other things, a visualization device and related systems and methods. Each of the aspects disclosed herein may include one or more of the features described in connection with any of the other disclosed aspects.

In one aspect of the present disclosure, a visualization device may include an image sensor, a lens for focusing light onto the image sensor, a first end, a second end opposite the first end, a lateral wall surface extending between the first end and the second end, and a coating on the lateral wall surface. The coating may include at least one of an electrically-insulating layer and a light-blocking layer, and may be deposited on the lateral wall surface using any method of deposition, including, but not limited to, physical vapor deposition (PVD).

Aspects of the visualization device may include one or more of the features below. The coating may include both the electrically-insulating layer and the light-blocking layer. The electrically-insulating layer may be deposited on the lateral wall surface and the light-blocking layer may be deposited on the electrically-insulating layer. The electrically-insulating layer may include titanium dioxide. The light-blocking layer may include pure titanium. The coating may include both the electrically-insulating layer and the pure titanium light-blocking layer, and the electrically-insulating layer may include titanium dioxide. The titanium dioxide layer may be deposited on the lateral wall surface and the pure titanium layer may be deposited on the titanium dioxide layer. The visualization device may further include at least one layer of glass. The at least one layer of glass may include a first layer of glass at the first end, and a second layer of glass at the second end. Lateral wall surfaces of the first and second layers of glass may form portions of the lateral wall surface of the visualization device. The lateral wall surface may be one of a plurality of lateral wall surfaces, and each of the lateral wall surfaces may have the coating thereon. The electrically-insulating layer may prevent electricity from flowing out of and/or into the lateral wall surface. The light-blocking layer may be opaque.

In another aspect of the present disclosure, a system for facilitating deposition of a coating on a visualization device may include a post having a first end, a second end, and a central longitudinal axis. The system may also include a first member coupled to the post. The first member may include a through hole. The system may also include a second member coupled to the post. The second member may be closer to the second end of the post than the first member. The system may also include a pin slidably received in the through hole. The pin may be slidable through the through hole and toward the second member to secure, when in use, the visualization device against the second member. The post may be rotatable about the central longitudinal axis to rotate the first member, second member, pin, and visualization device about the central longitudinal axis.

Aspects of the system may also include one or more of the features below. The visualization device may be one of a plurality of visualization devices, the through hole may be one of a plurality of through holes, the pin may be one of a plurality of pins. Each of the pins may be slidably received in one of the through holes to secure one of the visualization devices against the second member. The first member may include an arm extending radially outward from the central longitudinal axis, and the through hole may extend through the arm. A cross-sectional shape of a portion of the pin may be complementary to a cross-sectional shape of the through hole. The cross-sectional shape of the portion of the pin may have a straight side and/or may be polygonal.

In yet another aspect of the present disclosure, a method of coating a visualization device may include providing a masking material to a first end of the visualization device. The method may also include providing the masking material to a second end of the visualization device. The method may further include depositing a coating on the visualization device. The coating may include at least one of an electrically-insulating layer and a light-blocking layer. The method may also include removing the masking material, and portions of the coating on the masking material, from the first and second ends, while leaving the coating on a lateral wall surface of the visualization device that extends between the first and second ends.

Aspects of the method may also include one or more of the features below. The masking material may include ink. Removing the ink may include applying isopropyl alcohol to the ink to dissolve the ink, thereby removing the portions of the coating on top of the ink.

It may be understood that both the foregoing general description and the following detailed description are exemplary and explanatory only and are not restrictive of the features claimed.

As used herein, the terms "comprises," "comprising," or any other variation thereof, are intended to cover a non-exclusive inclusion such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn to a visualization device that has a coating, related systems to facilitate application (via, e.g., deposition) of the coating, and method steps performed to apply the coating. Though the coating is deposited in the described embodiments, the coatings disclosed herein may be applied by any suitable method. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient. The term "approximately," when used to describe a numerical value, may be anywhere in a range of ±5% from the numerical value.

Figure 1A:
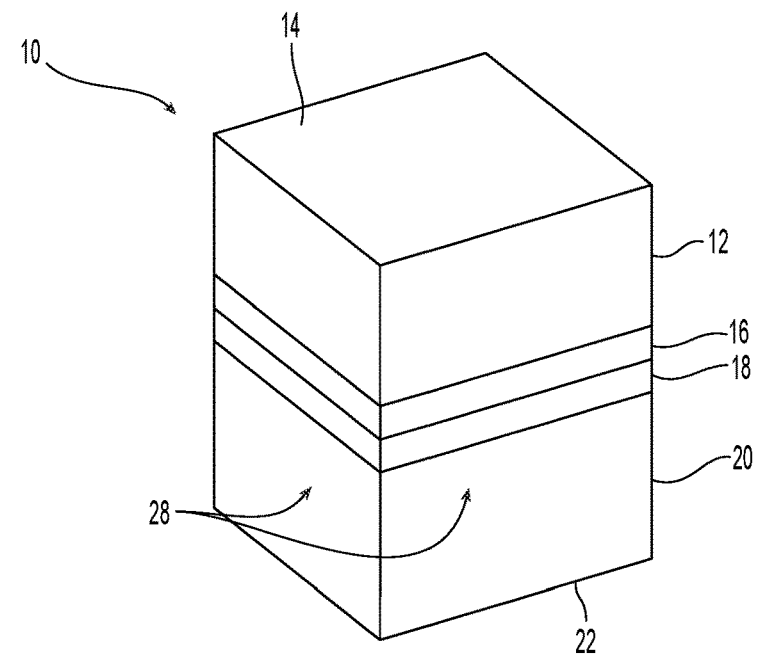
FIG. 1A is a perspective view of a visualization device, in accordance with aspects of the present disclosure.
Figure 1B:
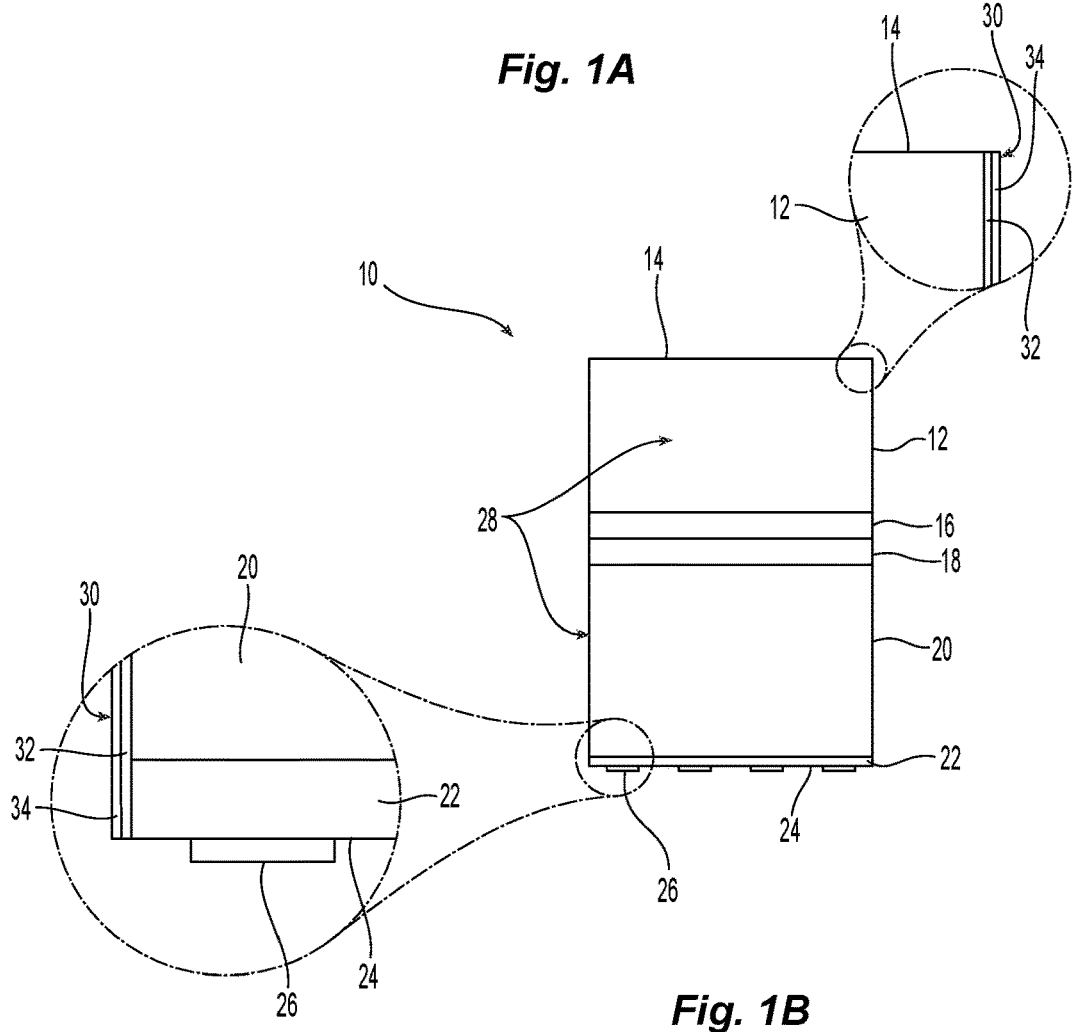
FIG. 1B is a side view of the visualization device of FIG. 1A, in accordance with aspects of the present disclosure.

FIGS. 1A and 1B show aspects of a visualization device 10. According to one aspect, visualization device 10 may include multiple components/layers in a stack. One of the components may be a cover 12 forming a distal layer at a distal end of visualization device 10. Cover 12 may be made of any suitable transparent or translucent material including, for example, borosilicate glass. Light may enter a distal surface 14 of cover 12, and may pass therethrough in a path toward a proximal end of visualization device 10. An aperture 16 may receive light from cover 12. Aperture 16 may be opaque at its periphery, but may include a transparent or translucent circular central portion (not shown), or may include a central circular opening (not shown), such that light from cover 12 may pass through the central portion into a lens 18, where the light may be focused. The focused light from lens 18 may enter an interface 20 that may have features similar to cover 12. The focused light passing through interface 20 may reach an image sensor 22. Image sensor 22 may include, for example, a complementary metal-oxide semiconductor (CMOS) image sensor. Image sensor 22 may form a proximal layer at a proximal end of visualization device 10.

A proximal surface 24 of image sensor 22 may have a contact 26 thereon in the form of an electrode and/or solder pad. It is contemplated that multiple contacts may be provided, each with features similar to contact 26. Contact 26 may connect image sensor 22 to a wire or wires (not shown). Image sensor 22 may receive light, generate output signals, and transmit the output signals to a display device (not shown) via the wire/wires for viewing by a user.

Visualization device 10 also may include additional layers between the aforementioned layers. The additional layers may include, for example, a spacer layer and/or a bond layer. Alternatively, it is also contemplated that visualization device 10 may include fewer layers than the ones described above to, for example, help reduce its dimensions.

Visualization device 10 may include a sidewall 28 extending longitudinally between its proximal and distal ends. Sidewall 28 may be formed, for example, by side surfaces of each of the aforementioned layers once they are stacked to form visualization device 10. If left uncovered, light may enter sidewall 28, potentially resulting in unwanted light saturation. The performance of visualization device 10 may be enhanced by reducing or eliminating unwanted light saturation, allowing image sensor 22 to receive light coming exclusively (or substantially exclusively) from the distal end of visualization device 10 with little or no interference.

A coating 30 may be applied to sidewall 28 to limit or eliminate unwanted light saturation. Coating 30 may include one or more layers of material. For example, coating 30 may include an inner layer 32 and an outer layer 34. Inner layer 32 may be applied directly onto sidewall 28, and outer layer 34 may be applied onto inner layer 32. Inner and outer layers 32 and 34 may be composed of any suitable material. For example, one of or both of inner and outer layers 32 and 34 may be composed of alumina or aluminum. In some examples, inner and outer layers 32 and 34 may be applied consecutively and within the same process equipment.

As another example, inner layer 32 may be composed of a ceramic layer of titanium dioxide and/or outer layer 34 may be composed of titanium. Titanium dioxide may be electrically insulating, allowing inner layer 32 to act as an insulating layer to, for example, protect visualization device 10 from electrical shorting risks. Titanium may help block light, allowing outer layer 34 to act as a light blocking layer for reducing or eliminating unwanted light saturation through sidewall 28. Additional layers (not shown) of similar or different materials may also be applied as part of coating 30. Exemplary light blocking materials may include, but are not limited to, gold, aluminum, niobium, silver, copper, chromium, indium, molybdenum, stainless steel, tungsten, nickel, zinc, metal oxides, metal nitrides, and/or various alloys.

Inner layer 32 and/or outer layer 34 may be deposited on sidewall 28 by any suitable method, such as, e.g., thermal oxidation, chemical vapor deposition ("CVD"), and/or physical vapor deposition ("PVD"). PVD encompasses a variety of vacuum deposition methods that may be used to deposit thin coatings by the condensation of a vaporized form of a desired coating material onto a surface. One form of PVD is sputtering, in which a glow plasma discharge bombards a material, thereby sputtering some away as a vapor for subsequent deposition onto a surface. Inner layer 32 may be sputtered onto sidewall 28, and outer layer 34 may subsequently be sputtered onto inner layer 32.

According to one example, a mixture of argon gas and oxygen gas may be introduced into a PVD chamber during sputtering of the titanium. The argon gas may facilitate formation of the plasma, and the oxygen gas may react with the sputtered titanium, resulting in the deposition of titanium dioxide on sidewall 28. Subsequently, the gas mixture in the PVD chamber may be replaced with pure argon gas, such that sputtering of the titanium deposits a layer of pure titanium on top of the titanium oxide layer. PVD may deposit the layers with a thickness of 500 and 10,000 angstroms. The layers may have a consistent thickness throughout. Conventional light blocking paint, on the other hand, may have a layer thickness of approximately 50,000 to 200,000 angstroms.

Care may be taken to ensure that coating 30 does not cover distal surface 14 of cover 12, so that light may freely pass through distal surface 14. Care also may be taken to ensure that coating 30 does not cover proximal surface 24 of image sensor 22 and/or contact 26, since covering proximal surface 24 and/or contact 26 may hinder the transmission of output signals from image sensor 22 to their destination, and may hinder power distribution in and/or to image sensor 22. A mask (not shown) may be applied to distal surface 14, proximal surface 24, and/or contact 26 to keep them free of coating 30. For example, prior to the performance of PVD to coat visualization device 10, a layer of masking material, such as ink or paint, may be applied to distal surface 14, proximal surface 24, and/or contact 26. The ink may be applied using a spray-coating system, marker, and/or brush, among other modes of application. While PVD is taking place, coating 30 may be applied on top of the ink. After coating the outer surfaces of visualization device 10 and the masking material with PVD, a solvent, such as isopropyl alcohol or water, may be applied onto the outer surfaces of visualization device 10. The solvent may remove the ink or paint, and along with it the portions of coating 30 on top of the ink, thus leaving sidewall 28 of visualization device 10 coated and distal surface 14, proximal surface 24, and/or contact 26 uncoated. Additionally or alternatively, laser energy may be directed at portions of coating 30 on top of the ink or paint to ablate or otherwise remove those portions. Alternatively, the step of applying masking material may be skipped, and laser energy may be directed at distal surface 14, proximal surface 24, and/or contact 26 to remove portions of coating 30 thereon.

Figure 2A:
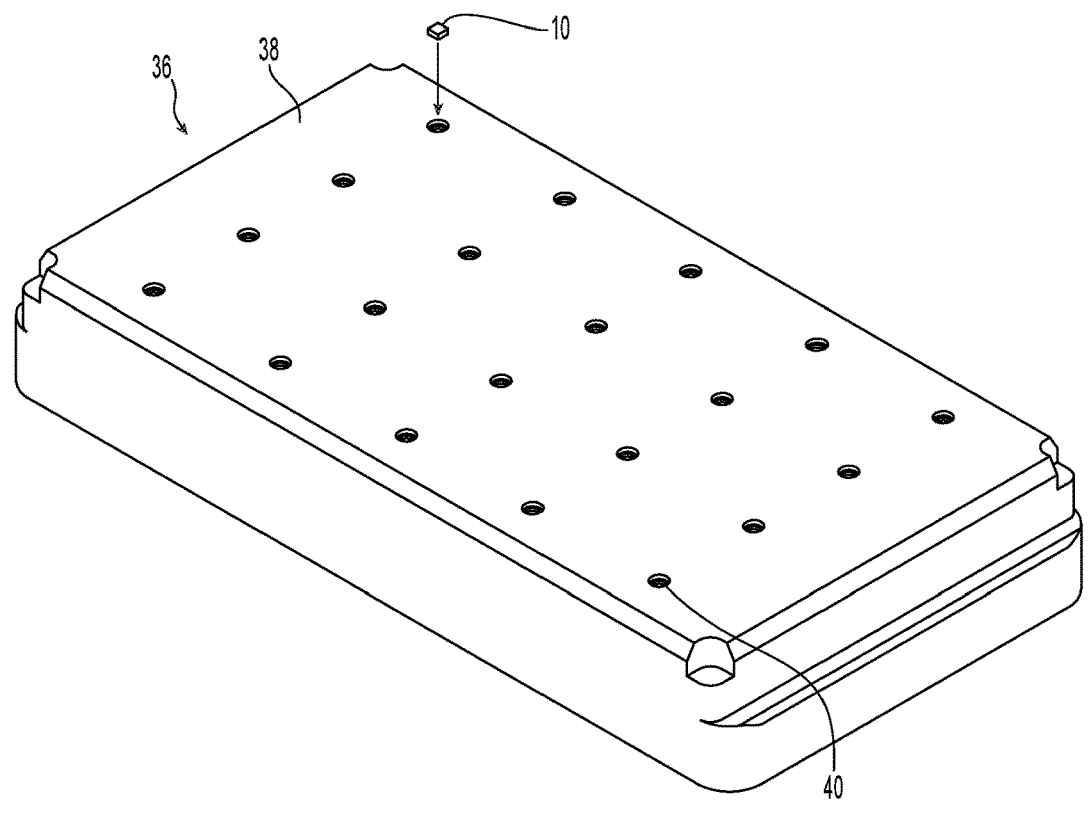
FIG. 2A is a perspective view of a holder of a system for coating a visualization device, in accordance with aspects of the present disclosure.
Figure 2B:
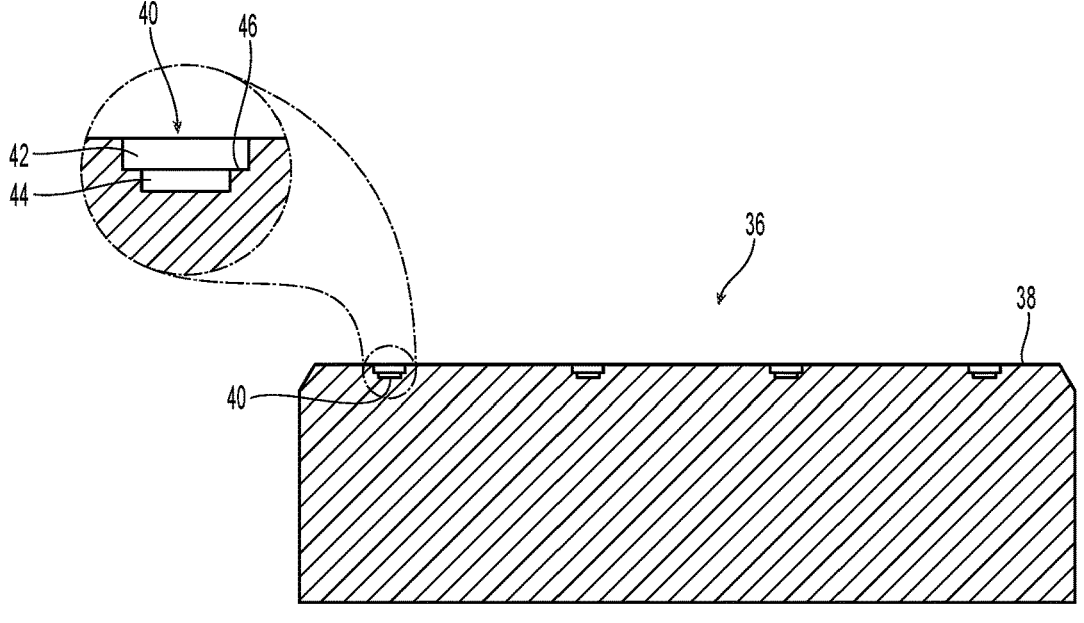
FIG. 2B is a cross-sectional view of the holder of FIG. 2A, in accordance with aspects of the present disclosure.

FIGS. 2A and 2B show aspects of a holder 36 that may be used to secure visualization device 10 during the PVD coating process. Holder 36 may be made of any suitable material including, for example, a solid block of aluminum. An upper surface 38 of holder 36 may have a recess 40 formed therein. Recess 40 may have an upper recess portion 42 and a lower recess portion 44. Upper recess portion 42 and lower recess portion 44 may be differently sized. For example, upper recess portion 42 may have a greater width than lower recess portion 44, forming an intermediate surface 46 at the junction between upper and lower recess portions 42 and 44. Additionally or alternatively, upper recess portion 42 may have a greater height than lower recess portion 44. While a single recess 40 is described above, it should be understood that holder 36 may include a plurality of recesses, similar to recess 40, for simultaneously securing a plurality of visualization devices that are similar to visualization device 10. The plurality of recesses may be arranged in rows and/or columns on upper surface 38. Adjacent recesses may be spaced from one another to allow each of the visualization devices to be coated without unduly interfering with adjacent visualization devices.

As visualization device 10 is inserted into recess 40 with the distal end of visualization device 10 facing recess 40, distal surface 14 of cover 12 may eventually come into contact with intermediate surface 46. Through this contact, intermediate surface 46 may prohibit further insertion of visualization device 10 into recess 40, leaving a proximal portion of visualization device 10 protruding above upper surface 38 of holder 36. Lower recess portion 44 may remain empty. Conversely, as visualization device 10 is inserted into recess 40 with the proximal end of visualization device 10 facing recess 40, proximal surface 24 of image sensor 22 may eventually come into contact with intermediate surface 46, thus preventing further insertion and leaving a distal portion of visualization device 10 protruding above upper surface 38. Contact 26 may extend into lower recess portion 44.

Upper recess portion 42 and lower recess portion 44 may be dimensioned with tight tolerances relative to visualization device 10, to firmly secure visualization device 10 when portions of visualization device 10 are inserted therein. It should be understood that the dimensions may vary based on the characteristics of the visualization devices being secured by holder 36.

Holder 36 may also be used to secure visualization device 10 during masking. Visualization device 10 may be inserted into recess 40 proximal end first. The distal end of visualization device 10 may project from upper surface 38 of holder 36. The mask (e.g., ink) may be applied to distal surface 14 of cover 12. Once the mask has dried or otherwise set on distal surface 14, visualization device 10 may be flipped and inserted into recess 40 distal end first. With the proximal end of visualization device 10 projecting from upper surface 38 of holder 36, the mask may be applied to proximal surface 24 of holder 36 and/or contacts 26. The masks also may be applied in reverse order. Similar steps may be used to remove the masks, and portions of coating 30 thereon, after coating 30 has been applied.

Holder 36 may also be used to secure visualization device 10 during PVD application. Visualization device 10 may be flipped one or more times to ensure that sidewall 28 of visualization device 10 is fully coated. For example, with a first end of visualization device 10 received in recess 40 and a second end of visualization device 10 protruding from upper surface 38 of holder 36, holder 36 may pass through a PVD chamber (not shown). In the PVD chamber, inner layer 32 of coating 30 may be deposited on at least portions of sidewall 28 associated with the protruding second end of visualization device 10. Once inner layer 32 has set, holder 36 may be removed from the PVD chamber, and visualization device 10 may be flipped such that the second end of visualization device 10 is received in recess 40 and the first end of visualization device 10 protrudes from upper surface 38. Holder 36 may re-enter PVD chamber, where inner layer 32 may be deposited on at least the uncoated portions of sidewall 28. Similar steps may be used to apply outer layer 34 of coating 30 onto sidewall 28.

Because visualization device 10 may be held on holder 36 by its own weight, and/or by its contact with surfaces of holder 36 that form recess 40, holder 36 may be suitable for securing visualization device 10 during a low-speed and/or linear path through the PVD chamber. Increasing the speed of holder 36 and/or introducing changes of direction in the path of holder 36 may cause visualization device 10 to be jostled out of recess 40 of holder 36. Securement of visualization device 10 to holder 36 may be improved by, for example, ensuring that the dimensions of visualization device 10 and of recess 40 are approximately complementary, or at least close enough to limit movement of visualization device 10 within recess 40. It is also contemplated that holder 36 may include one or more lips or ledges at its end portions to facilitate mounting of holder 36 on a conveying device (not shown), such as a shuttle, designed to convey holder 36 through the PVD chamber.

Figure 3A:
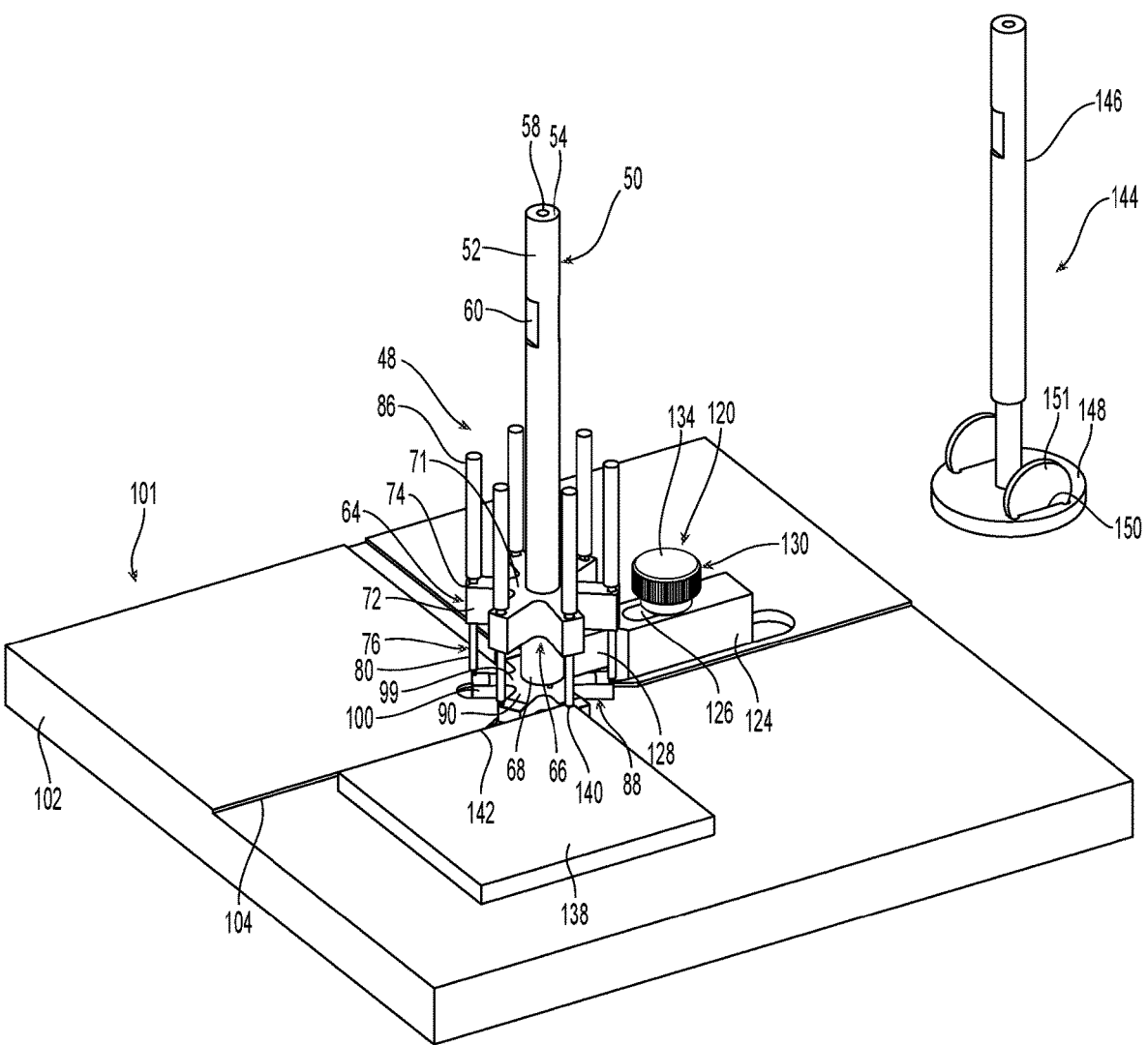
FIG. 3A is a perspective view of an assembly forming part of a system for coating a visualization device, in accordance with aspects of the present disclosure.
Figure 3B:
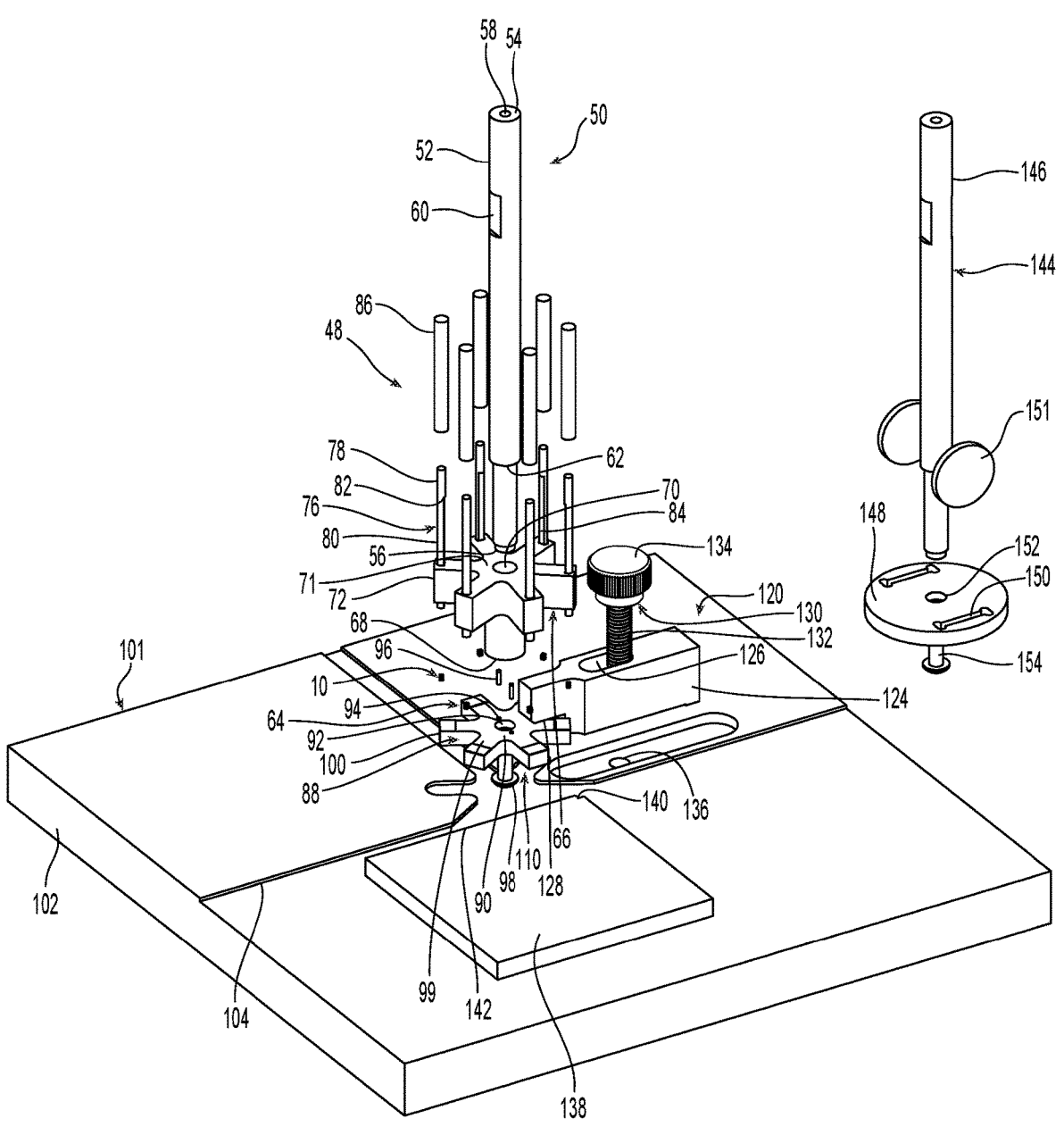
FIG. 3B is an exploded perspective view of the assembly of FIG. 3A, in accordance with aspects of the present disclosure.

FIGS. 3A and 3B show aspects of a holding assembly 48 for holding visualization device 10 with a clamping force. Holding assembly 48 may include a mounting post 50. Post 50 may include a rod or mandrel having an upper end 54 and a lower end 56. Post 50 also may include a central lumen or through hole 58 extending therethrough. Hole 58 may have one or more threaded portions (not shown). For example, hole 58 may include threaded portions at upper and lower ends 54 and 56 to facilitate securement of post 50 to other components. It is contemplated that other suitable forms of securement, in addition to or as an alternative to threaded engagement, may be used.

Upper end 54 of post 50 may be secured to a drive system (not shown). The drive system may rotate post 50 about the central longitudinal axis of post 50. Additionally or alternatively, the drive system may rotate post 50 about an axis parallel to the central longitudinal axis of post 50. The parallel axis may also move linearly or may orbit yet another parallel axis. When two types of rotation are present, post 50 may be described as undergoing double planetary rotation. The drive system may move post 50, and components supported thereon (including, as described in more detail below, a holding mechanism 64 and visualization device 10) through a PVD chamber (not shown). Using double planetary rotation may allow coating 30 to be applied to visualization device 10 in a smaller PVD chamber than would otherwise be the case. Post 50 may be secured to the drive system by a threaded fastener (not shown) extending from the drive system into hole 58 of post 50. Additionally or alternatively, post 50 may be secured to the drive system by engagement between the drive system and a flattened portion 60 of post 50. A second flattened portion (not shown) may also be provided for similar purposes on a surface of post 50 diametrically opposed to flattened portion 60.

The lower portion of post 50 may have a reduced diameter in comparison to the upper portion of post 50, forming a shoulder or abutment 62 between the two portions. The reduced diameter of the lower portion of post 50 may be sized to receive holding mechanism 64, which may in turn secure visualization device 10. While securement of one visualization device 10 is described, it should be understood that holding mechanism 64 may also hold additional visualization devices, similar to visualization device 10, simultaneously.

Holding mechanism 64 may include a pin alignment member 66. Pin alignment member 66 may include a stem 68. Stem 68 may be cylindrical. A central through hole 70 may extend through stem 68. The upper end of pin alignment member 66 may be defined by an upper surface 71. Hole 70 may receive the distal portion of post 50, allowing pin alignment member 66 to slide up onto and around post 50 until upper surface 71 contacts abutment 62 of post 50.

At the upper end of stem 68, an arm 72 may extend radially outwardly from the central longitudinal axis of stem 68. While one arm 72 is described here, it should be understood that a plurality of arms may extend from stem 68 as shown in FIGS. 3A and 3B, with each of the arms being similar to arm 72. Moreover, while six arms are depicted in FIGS. 3A and 3B, it should be understood that more or fewer arms may be provided. It is also contemplated that a radially-outermost surface of arm 72 may be convex.

Arm 72 may have an upper surface coplanar with upper surface 71. Additionally or alternatively, arm 72 may have a generally rectangular cross-sectional shape. Arm 72 may also include a peripheral through hole 74. Hole 74 may have an irregular cross-sectional shape. For example, hole 74 may have a cross-sectional shape that is partially curved (e.g., partially circular) and partially straight, to serve as an anti-rotation feature, as will be described in more detail below. Alternatively, hole 74 may have a polygonal cross-sectional shape to, amongst other things, limit or eliminate rotation. Alternatively still, hole 74 may have a circular cross-sectional shape. Hole 74 may be centered on a centerline of arm 72, or may be offset from the centerline of arm 72.

Holding mechanism 64 may also include a pin 76. Pin 76 may include an upper portion 78 and a lower portion 80. A cross-sectional area of upper portion 78 may be greater than a cross-sectional area of lower portion 80. Additionally or alternatively, a width of upper portion 78 may be greater than a width of lower portion 80. The difference is cross-sectional area and/or width provides pin 76 with a shoulder or abutment 82. It is contemplated that, for example, the cross-section of upper portion 78 may be circular and/or the cross-section of lower portion 80 may be D-shaped.

Lower portion 80 of pin 76 may be sized and shaped to be slidably received in hole 74 of arm 72. Lower portion 80, therefore, may be inserted into the upper end of hole 74, and may slide down into hole 74 until abutment 82 makes contact with upper surface 71 of pin alignment member 66 at, for example, a corner portion of arm 72. The cross-sectional shape of lower portion 80 may be complementary to the cross-sectional shape of hole 74, which in some instances, may mean that the cross-sectional shape of lower portion 80 may be partially curved (e.g., partially circular) and partially straight, or polygonal. Straight or polygonal sides of lower portion 80 may engage straight or polygonal sides of hole 74 to limit or eliminate rotation of pin 76 relative to hole 74. This limiting/elimination may help secure visualization device 10, as described in more detail below. Alternatively, pin 76 may have a circular cross-sectional shape which, when slidably received in a similarly shaped hole 74, may allow pin 76 to slide and rotate within peripheral through hole 74.

Pin 76 may include a blind bore (not shown) extending up from its lower surface. The blind bore may have a rectangular cross-sectional shape. Additionally or alternatively, the blind bore may be sized to receive contacts 26 as the lower surface of pin 76 engages proximal surface 24 of image sensor 22, as will be described in greater detail below. While one pin 76 is described here, it should be understood that a plurality of pins may be provided as shown in FIGS. 3A and 3B, with each of the pins being similar to pin 76. Moreover, while six pins are depicted in FIGS. 3A and 3B, it should be understood that more or fewer pins may be provided depending on the number of arms of pin alignment member 66.

Holding mechanism 64 may also include a cover 86 for mounting on pin 76. Cover 86 may be cylindrical, and may include a blind hole (not shown) extending up from its lower surface. Upper portion 78 of pin 76 may be cylindrical, and may be received in the blind hole. Cover 86 may slide onto upper portion 78 until the upper end of pin 76 reaches the closed end of the blind hole. Abutment 82 of pin 76 may remain exposed outside of cover 86 when the upper end of pin 76 and the closed end of the blind hole make contact. Cover 86 may act as a weight to facilitate sliding of pin 76 down into hole 74. For example, the additional weight provided by cover 86 may help pin 76 overcome any frictional engagement between the outer surface of pin 76 and the surface of arm 72 forming hole 74. Where multiple pins are provided, one or more of the pins may receive a cover similar to cover 86, as shown in FIGS. 3A and 3B.

Holding mechanism 64 may further include an end plate 88. End plate 88 may have a central body 90 including a central through hole 92. Hole 92 may receive lower end 56 of post 50, allowing end plate 88 to slide onto the lower portion of post 50 and up the lower portion until an upper surface 99 of end plate 88 contacts the surface forming the lower end of stem 68 of pin alignment member 66. A fastener 98 may engage both the lower surface of end plate 88 and the lower end of hole 58 of post 50 to secure end plate 88 and pin alignment member 66 onto the lower portion of post 50. The lower surface of end plate 88 may have a blind recess 40 formed therein that may receive the lower end of fastener 98, such that the lower end of fastener 98 may be flush with the lower surface of end plate 88.

An arm 100, or a plurality of arms similar to arm 100, may extend radially outward from central body 90. Arm 100 may have a rectangular cross-sectional shape. In one example, arm 100 may be similar in size and shape to arm 72 of pin alignment member 66. Radially outer portion of arm 100 may include surface texturing for securing objects in contact with the surface and/or a raised or lowered region for positioning visualization device 10.

Central body 90 of end plate 88 may also include a blind bore 94 extending downward from its upper surface 99. Blind bore 94 may receive a lower portion of an alignment pin 96. An upper portion of alignment pin 96 may be received in a blind bore (not shown) extending up from the surface forming the lower end of stem 68. Inserting alignment pin 96 into the aforementioned blind bores may align pin alignment member 66 and end plate 88, and in particular, arms 72 and 100 of pin alignment member 66 and end plate 88, respectively. When pin alignment member 66 and end plate 88 are aligned, pin 76 may slide downwardly relative to arm 72 toward a corner portion of arm 100. Pin 76 may clamp visualization device 10 against upper surface 99 of end plate 88 at the corner portion of arm 100. While a single pair of blind bores and pin 96 is described herein, it should be understood that a plurality of pairs of blind bores and a plurality of corresponding pins may be provided to help align end plate 88 and pin alignment member 66. It is contemplated that arm 72 and arm 100 may be vertically aligned when pin alignment member 66 and end plate 88 are aligned. Alternatively, arm 72 may be offset from arm 100 when pin alignment member 66 and end plate 88 are aligned.

The anti-rotation features of pin 76 and hole 74 may limit or prevent pin 76 from rotating relative to hole 74. Rotation of pin 76 may, for example, cause movement of visualization device 10, twisting or otherwise, that may cause visualization device 10 to fall free of holding mechanism 64. For at least this reason, rotation of pin 76 relative to hole 74 may be avoided.

FIGS. 3A and 3B also show aspects of a loading assembly 101 for loading visualization device 10 onto end plate 88 for clamping by pin 76. Loading assembly 101 may include a base 102 having vertical guide surfaces 104 that form slots on base 102. Vertical guide surfaces 104 may engage side surfaces of end plate 88 to hold end plate 88 in a predetermined orientation on base 102. For example, vertical guide surfaces 104 may engage side surfaces of arm 100 of end plate 88. Holding assembly 48 may be lowered onto base 102 until end plate 88 contacts base 102, and end plate 88 may be rotated or otherwise adjusted until arm 100 of end plate 88 fits between vertical guide surfaces 104. Where multiple arms are provided on end plate 88, vertical guide surfaces 104 may form slots for some or all of the arms, to orient end plate 88 on base 102, as shown in FIGS. 3A and 3B.

Vertical guide surfaces 104 may also receive a clamp 120. Clamp 120 may include a body 124. A width of body 124 may correspond to a distance between opposing vertical guide surfaces 104. Body 124 may have a protrusion 128 extending laterally therefrom. Protrusion 128 may extend over and engage upper surface 99 of end plate 88 when both body 124 and end plate 88 are properly oriented on base 102. According to one example, the lower surface of protrusion 128 may be offset vertically from the lower surface of body 124 to receive end plate 88.

Base 102 may also include a slot 126. Slot 126 may receive a fastener 130 of clamp 120. Fastener 130 may have a stem 132 and a head 134. Stem 132 may be received in, and secured in, a bore 136 formed in a surface of base 102.

In use, when end plate 88 is positioned on base 102, body 124 of clamp 120 may be placed between vertical guide surfaces 104 and guided to position protrusion 128 onto upper surface 99 of end plate 88 and in between adjacent arms 100. Stem 132 of fastener 130 may be inserted through slot 126 in body 124, and into bore 136 in base 102. Stem 68 and bore 136 may be threaded so as to couple to one another via threaded engagement. Head 134 of fastener 130 may be rotated to move stem 68 deeper into bore 136, and enhance engagement between head 134 and the upper surface of body 124, thereby firmly securing body 124 onto base 102. With clamp 120 in place, loading assembly 101 may be ready to receive visualization device 10.

A block 138 may be used to help position visualization device 10 on arm 100 of end plate 88 in a position where visualization device 10 may be clamped between end plate 88 and pin 76. For example, one side of block 138 may be pressed against one of vertical guide surfaces 104. Block 138 may be slidably moved in a transverse direction along vertical guide surface 104 until a cutout 140, formed at a corner of block 138, engages a corner of arm 100. Cutout 140 may be formed, for example, by removing a square-shaped portion out of the corner of block 138. Cutout 140 may have a length and a width of approximately about 1 to about 2 millimeters.

A tool (not shown) used to hold visualization device 10, such as a forceps or suction device, may be guided downward along the surfaces of block 138 forming cutout 140 until visualization device 10 contacts upper surface 99 of arm 100. Visualization device 10 may then be released. Additionally or alternatively, visualization device 10 may be placed on upper surface 99 of end plate 88, and slid sideways into cutout 140 such that a corner of visualization device 10 engages the inverted corner formed by cutout 140.

With visualization device 10 in place, pin 76 may be lowered to clamp visualization device 10 against upper surface 99 of end plate 88. It is contemplated that end plate 88 may engage distal surface 14 of cover 12, and pin 76 may engage proximal surface 24 of image sensor 22, leaving sidewalls 28 of visualization device 10 exposed. Further, pin 76 and end plate 88 may mask distal surface 14 and contacts 26 of visualization device 10 during the PVD process, and thus, the step of applying a mask onto distal surface 14 and contacts 2 may be skipped.

After visualization device 10 is clamped, clamp 120 may be removed. When multiple visualization devices are provided, loading assembly 48 may be lifted, rotated, and then lowered back onto base 102 to load another visualization device. Clamp 120 may be re-applied to hold end plate 88 in its new orientation. Block 138 may be used, using the above-outlined steps, to facilitate placement of the other visualization device on another arm of end plate 88. The pin aligned with that arm may be lowered to clamp the visualization device. These steps may be repeated until visualization devices are clamped to each of the arms of end plate 88.

Once the visualization devices are clamped, clamp 120 may be removed and loading assembly 48 may be coupled to the drive system (not shown) and placed into the PVD chamber (also not shown). In the PVD chamber, inner layer 32 of coating 30 may be applied while the drive system moves holding assembly 48 through the PVD chamber with double planetary rotation. Inner layer 32 may be deposited on sidewall 28 of visualization device 10. Once inner layer 32 has been deposited, outer layer 34 of coating 30 may be applied while the drive system once again moves loading assembly 101 through the PVD chamber with double planetary rotation. Outer layer 34 may be deposited over sidewall 28 on top of inner layer 32. Distal surface 14 of cover 12 and contacts 2 of image sensor 22 may remain uncoated due to distal surface 14 and contacts 2 being covered by the upper surface of end plate 88 and the lower end of pin 76, respectively, during coating.

FIGS. 3A and 3B also show aspects of a testing assembly 144 for determining properties of coating 30. Testing assembly 144 may include a post 146 similar to post 50 of holding assembly 48. Testing assembly 144 may also include an end plate 148 securable to post 146 by a fastener 154. End plate 148 may include an opening 152 for receiving post 146 and fastener 154, and a slot 150 for receiving a test disk or blank 151. Blank 151 may be made of aluminum, an aluminum alloy like aluminum oxide, or any other suitable material. Slot 150 may include a rectangular central portion with enlarged ends, the enlarged ends facilitating placement of blank 151 into slot 150, and removal of blank 151 from slot 150.

Once testing assembly 144 is assembled, and blank 151 is inserted into slot 150, post 146 may be coupled to the same drive system as post 50. Testing assembly 144 may be taken through the PVD chamber with double planetary rotation in a path parallel to holding assembly 48. Blank 151 may receive the same coating 30 under the same conditions as visualization device 10. The coating 30 on blank 151 may be tested to determine properties including, for example, strength, thickness, and coverage. Testing coating 30 on visualization device 10 may therefore be avoided in case such testing may damage coating 30 and/or visualization device 10. It is contemplated that multiple slots may be provided for holding multiple blanks for additional testing.

Figure 4A:
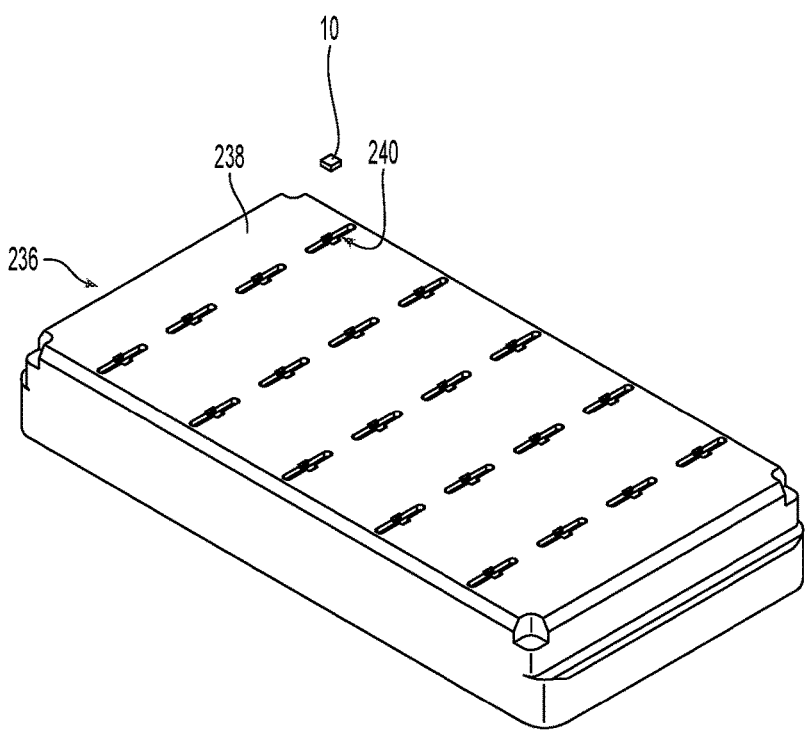
FIG. 4A is a perspective view of another holder used to hold the visualization device, in accordance with aspects of the present disclosure.
Figure 4B:
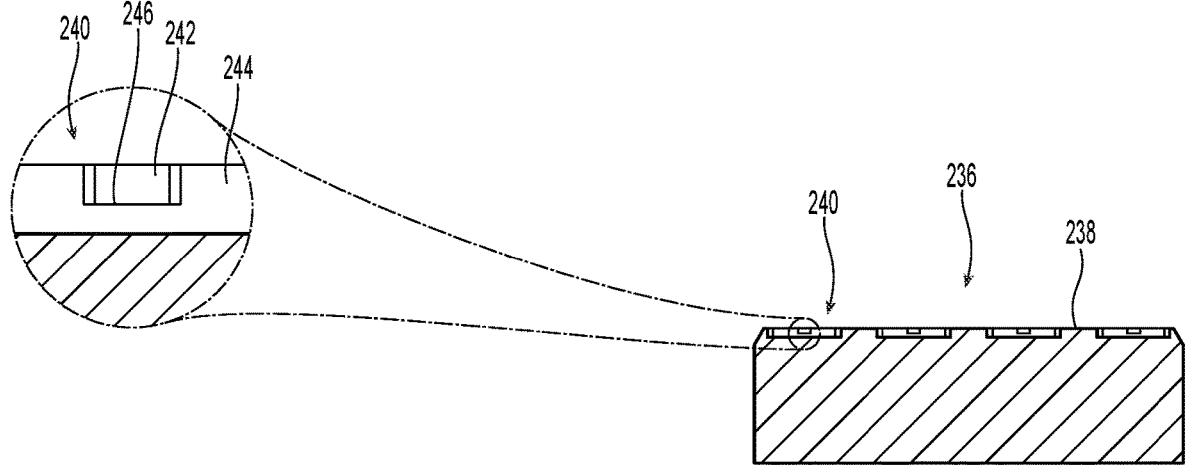
FIG. 4B is a cross-sectional view of the holder of FIG. 4A, in accordance with aspects of the present disclosure.

FIGS. 4A and 4B show aspects of a holder 236 that may be used to secure visualization device 10 during cleaning of visualization device 10 prior to the PVD coating process, and/or during the PVD coating process. Holder 236 may be made of any suitable material including, for example, a solid block of aluminum. An upper surface 238 of holder 36 may have a recess 240 formed therein. Recess 240 may have a central recess portion 242 and lateral recess portions 244. Central recess portion 242 and lateral recess portions 244 may be differently sized. For example, central recess portion 242 may have a greater width than lateral recess portions 244. Additionally or alternatively, central recess portion 242 may have a lesser height than lateral recess portions 244. The dimensional differences between central and lateral recess portions 242 and 244 may form an intermediate surface 246 at the junction between central and lateral recess portions 242 and 244. While a single recess 240 is described above, it should be understood that holder 236 may include a plurality of recesses, similar to recess 240, for simultaneously securing a plurality of visualization devices that are similar to visualization device 10. The plurality of recesses may be arranged in rows and/or columns on upper surface 238. Adjacent recesses may be spaced from one another to allow each of the visualization devices to be processed without unduly interfering with adjacent visualization devices.

As visualization device 10 is inserted into recess 240 with one sidewall 28 of visualization device 10 facing recess 240, that sidewall 28 may eventually come into contact with intermediate surface 246. Through this contact, intermediate surface 246 may prohibit further insertion of visualization device 10 into recess 240, leaving a portion of visualization device 10 protruding above upper surface 238 of holder 236. The protruding portion of visualization device 10 may include the opposite sidewall 28. The length and width of central recess portion 242 may be dimensioned with tight tolerances relative to visualization device 10, to firmly secure visualization device 10 when portions of visualization device 10 are inserted therein. Lateral recess portions 244 may accommodate prongs of a pair of tweezers (not shown), or some other instrument, as the tweezers are used to place visualization device 10 in central recess portion 242.

Holder 236 may also be used to secure visualization device 10 during cleaning. For example, with visualization device 10 secured in holder 236, laser energy may be directed at portions of visualization device 10 protruding out from recess 240. For example, laser energy may be directed at the horizontally-oriented sidewall 28 of visualization device 10, and/or vertically-oriented sidewalls 28 and surfaces of visualization device 10. The laser energy may remove foreign material, including glass particles, fibers, or other debris, from the surface(s) by, for example, ablating the debris. The laser energy may be provided by an excimer laser. The user may remove visualization device 10, rotate visualization device 10 (e.g., by 90, 180, and/or 270 degrees), re-insert visualization device 10 into recess 240, and direct laser energy at other surfaces of visualization device 10, to clean all sides of visualization device 10. After cleaning, the PVD application process may be performed to apply coating 30. If debris is present on surfaces of visualization device 10 during coating, the debris may cause pinhole leaks to form in the coating. For example, the debris may fall off after coating, leaving pinhole leaks in coating 30. Additionally or alternatively, the debris may be shaped such that it prevents coating 30 from being applied to certain areas. Cleaning visualization device 10 prior to applying coating 30 may reduce or eliminate pinhole leaks. Holder 236 may also be used to secure visualization device 10 during PVD application. Visualization device 10 may be flipped one or more times to ensure that sidewalls 28 of visualization device 10 are fully coated.

It will be apparent to those skilled in the art that various modifications and variations can be made in the disclosed systems and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A method of coating a visualization device, comprising:
providing a masking material to a first end of the visualization device;
providing the masking material to a second end of the visualization device;
depositing a coating on the visualization device, wherein the coating includes at least one of an electrically-insulating layer and a light-blocking layer, wherein the coating is deposited on the visualization device using physical vapor deposition (PVD) that comprises sputtering titanium within a PVD chamber;
securing the visualization device to a holding device by inserting the first end of the visualization device into a recess of the holding device in a first configuration or inserting the second end of the visualization device into the recess of the holding device in a second configuration before providing a masking material to the first or second ends of the visualization device or before depositing the coating on the visualization device; and
removing the masking material, and portions of the coating on the masking material, from the first and second ends, while leaving the coating on a lateral wall surface of the visualization device that extends between the first and second ends.

2. The method of claim 1, wherein the masking material includes ink, and removing the ink includes applying isopropyl alcohol to the ink to dissolve the ink, thereby removing the portions of the coating on top of the ink.

3. The method of claim 1, wherein the coating includes both the electrically-insulating layer and the light-blocking layer.

4. The method of claim 2, wherein the ink is applied using a spray-coating system, a marker, or a brush.

5. The method of claim 1, wherein a thickness of the coating is approximately 500 angstroms to approximately 10,000 angstroms.

6. The method of claim 1, wherein the visualization device further comprises an image sensor, a first layer of transparent material at the first end, and a second layer of the transparent material proximate the second end, wherein lateral wall surfaces of the image sensor, the first layer, and the second layer form portions of the lateral wall surface of the visualization device.

7. The method of claim 1, wherein an outer width of the visualization device is constant from the first end to the second end.

8. The method of claim 1, wherein the coating contacts an entirety of the lateral wall surface of the visualization device.

9. The method of claim 1, wherein removing portions of the coating on the masking material from the first and second ends includes applying laser energy to the coating on the masking material.

10. The method of claim 1, wherein titanium dioxide is deposited on the lateral wall surface of the visualization device to form the electrically-insulating layer when a mixture of argon gas and oxygen gas is introduced into the PVD chamber, and pure titanium is deposited on the electrically-insulating layer to form the light-blocking layer when the mixture of argon gas and oxygen gas is replaced with pure argon gas.

11. The method of claim 1, further comprising moving the visualization device between the first configuration and the second configuration after providing the masking material to the first or second ends of the visualization device or after depositing the coating on the visualization device.

12. The method of claim 1, further comprising:
moving the holding device with the visualization device in the first configuration into the PVD chamber;
removing the holding device from the PVD chamber after depositing the coating on the visualization device;
moving the visualization device from the first configuration to the second configuration; and
moving the holding device with the visualization device in the second configuration into the PVD chamber.

13. The method of claim 1, wherein dimensions of the recess of the holding device and dimensions of the visualization device are complementary.

14. The method of claim 1, wherein the holding device includes one or more ledges at end portions of the holding device to facilitate mounting of the holding device on a conveying device configured to move the holding device through the PVD chamber.

15. A method of coating a visualization device, comprising:
securing a plurality of visualization devices to a holding assembly, the holding assembly comprising a post having a first end, a second end, and a central longitudinal axis, a first member coupled to the post and engaging first ends of the plurality of visualization devices, the holding assembly further comprising a plurality of pins movable towards the first member to engage second ends of the plurality of visualization devices, leaving lateral wall surfaces extending between the first and second ends of the plurality of visualization devices exposed; and
depositing a coating on the lateral wall surfaces of the plurality of visualization devices, wherein the coating includes an electrically-insulating layer and a light-blocking layer.

16. The method of claim 15, wherein the post is rotatable about the central longitudinal axis to rotate the first member, the plurality of pins, and the plurality of visualization devices about the central longitudinal axis.

17. The method of claim 15, wherein the holding assembly further comprises a second member including a plurality of through holes, wherein the plurality of pins are slidable through the through holes.

18. The method of claim 15, wherein the first member includes a plurality of arms extending radially outward from the central longitudinal axis of the post, and radially outer portions of the plurality of arms include raised regions for positioning the plurality of visualization devices.

* * * * *